United States Patent [19]

Peck et al.

[11] Patent Number: 5,472,946

[45] Date of Patent: * Dec. 5, 1995

[54] TRANSDERMAL PENETRATION ENHANCERS

[76] Inventors: James V. Peck, 10821 Millington La.; Gevork Minaskanian, 11701 Lockport Ter., both of Richmond, Va. 23233

[*] Notice: The portion of the term of this patent subsequent to Feb. 28, 2006, has been disclaimed.

[21] Appl. No.: 103,504

[22] Filed: Aug. 6, 1993

Related U.S. Application Data

[63] Continuation-in-part of Ser. No. 912,086, Jul. 9, 1992, abandoned, which is a continuation of Ser. No. 179,144, Apr. 8, 1988, abandoned.

[51] Int. Cl.[6] ................................................ A61K 31/70
[52] U.S. Cl. ........................... 514/29; 514/24; 514/43; 514/946; 514/947
[58] Field of Search ........................... 514/29, 24, 42, 514/43, 44, 45, 946, 947

[56] References Cited

U.S. PATENT DOCUMENTS

| | | | |
|---|---|---|---|
| 4,177,278 | 12/1979 | Bossert et al. | 424/266 |
| 4,562,075 | 12/1985 | Rajadhyaksha | 514/788 |
| 4,568,343 | 2/1986 | Leeper et al. | 604/896 |
| 4,600,582 | 7/1986 | Stevens et al. | 424/91 |
| 4,600,583 | 7/1986 | Stevens et al. | 424/91 |
| 4,605,557 | 8/1986 | Stevens et al. | 424/91 |
| 4,808,414 | 2/1989 | Peck et al. | 424/449 |
| 4,837,026 | 6/1989 | Rajakhyaksha | 424/449 |
| 4,845,081 | 7/1989 | Sloan | 514/232.2 |
| 4,882,359 | 11/1989 | Nakagawa et al. | 514/947 |
| 4,902,676 | 2/1990 | Peck et al. | 514/29 |
| 4,960,771 | 10/1990 | Rajadhyaksha | 514/228.8 |
| 4,996,199 | 2/1991 | Minaskanian et al. | 514/167 |
| 5,043,441 | 8/1991 | Peck et al. | 540/526 |
| 5,045,317 | 9/1991 | Chess et al. | 424/401 |
| 5,118,676 | 6/1992 | Minaskanian et al. | 514/183 |
| 5,118,692 | 6/1992 | Peck | 514/317 |
| 5,128,376 | 7/1992 | Saito et al. | 514/772 |
| 5,234,959 | 8/1993 | Minaskanian et al. | 514/788 |

FOREIGN PATENT DOCUMENTS

| | | |
|---|---|---|
| 0241050 | 10/1987 | European Pat. Off. . |
| 8804938 | 7/1988 | WIPO . |

OTHER PUBLICATIONS

The Merck Index, (1976) ninth edition, pp. 302–303, 482, 541, 650, 719 and 1241.

*Primary Examiner*—Douglas W. Robinson
*Assistant Examiner*—Elli Peselev
*Attorney, Agent, or Firm*—Sterne, Kessler, Goldstein & Fox

[57] ABSTRACT

This invention relates to compounds and a method for their use in carrying physiologically active agents through body membranes such as skin and for retaining these agents in body tissues. More specifically, the invention relates to carboxylic acid derivatives and salts thereof, which compounds are useful in topically administering a physiologically active agent to a human or animal via a composition comprising the agent and an effective amount of a compound represented in one embodiment by the general formulae:

$$\begin{array}{c} W \\ \| \\ (CH_2)_x \quad N-\overset{R''}{\underset{H}{C}}-(CH_2)_n-R \\ Z \\ (CH_2)_m \quad R' \end{array}$$

wherein W represents oxygen, sulfur, or two hydrogen radicals;

Z represents oxygen, sulfur, or —$CH_2$—;

R represents alkyl optionally substituted with one to three double or triple bonds, —$SR'''$, —$OR'''$, —$NHR'''$, —$CH_3$, or $COOR_1$, and wherein $R_1$ represents hydrogen or lower alkyl;

R''' represents alkyl, alkylthioalkyl, alkoxyalkyl, substituted aminoalkyl, optionally substituted with a phenyl, benzoyl or heterocyclic group;

R' represents hydrogen, alkyl, alkoxy, acyloxy, alkylthio, hydroxy, —$(CH_2)_yCOOR_1$ and with y being between zero and 3, inclusive;

R'' represents hydrogen or —$(CH_2)_yCOOR_1$ such that when R'' is hydrogen, then W is two hydrogen radicals and R' is not hydrogen; and when R' is hydrogen, then R'' is not hydrogen;

and m is between one and 5, while n is between 1 and 24, and x is zero or 1, inclusive.

The invention further relates to the penetration-enhancing agents themselves and the method of making such penetration-enhancing agents.

13 Claims, No Drawings

TRANSDERMAL PENETRATION ENHANCERS

This application is a continuation-in-part of Ser. No. 07/912,086 filed Jul. 9, 1992 now abandoned, which is a continuation of Ser. No. 07/179,144 filed Apr. 8, 1988 now abandoned.

FIELD OF THE INVENTION

This invention relates to compositions comprising a physiologically active agent and a novel transdermal penetration enhancer in an amount effective to enhance the penetration of the physiologically-active agent through the skin or other membrane of the body of an animal.

BACKGROUND OF THE ART

Many physiologically active agents are best applied topically to obtain desirable results. Topical application, as contrasted to systemic application, can avoid metabolic degradation of the agents, largely avoids side effects of the agents, and permits high local concentrations of the agents.

The greatest problem in applying physiologically active agents topically is that the skin is a very effective barrier to penetration. The epidermis of the skin has an exterior layer of dead cells called the stratum corneum, which is tightly compacted and oily and which provides an effective barrier against gaseous, solid or liquid chemical agents, whether used alone or in water or oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use to treat such conditions as inflammation, acne, psoriasis, herpes simplex, eczema, infections due to fungus, virus or other microorganisms, or other disorders and conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellents and the like.

Physiologically active agents may be applied to locally affected parts of the body through the vehicles system described herein. Vehicles such as USP cold cream, ethanol and various ointments, oils, solvents, and emulsions have been used heretofore to apply physiologically active ingredients locally. Most such vehicles are not effective to carry significant amounts of physiologically active agents through the skin. One such vehicle is dimethyl sulfoxide.

The 1-lower alkyl substituted azacyclopentan-2-ones having 1–4 carbon atoms in the alkyl group are known to moderately enhance percutaneous absorption of chemicals, e.g. drugs. It was earlier recognized that it would be desirable to obtain the same or higher level of percutaneous absorption with substantially lower concentrations of the penetration-enhancing compound. Therefore, various N-substituted azacycloalkan-2-ones were invented having the desired properties. These new penetration-enhancing agents are described in U.S. Pat. Nos. 3,989,815; 3,989,816; 3,991,203; 4,122,170; 4,316,893; 4,405,616; 4,415 563; 4,423,040; 4,424,210; and 4,444,762, which are hereby incorporated by reference.

It is an object of this invention to provide new penetration-enhancing agents having the desirable property of enhancing the percutaneous absorption of physiologically-active agents at concentrations lower than the 1-lower alkyl substituted azacyclopentan-2-ones.

It is also an object of this invention to provide penetration-enhancing agents that are equivalent to the aforesaid new penetration-enhancing agents described in the above U.S. patents.

Other objects and advantages of the instant invention will be apparent from a careful reading of the specification below.

In this description, the term "animal" includes human beings as well as other forms of animal life, and especially domesticated animals and pets.

SUMMARY OF THE INVENTION

This invention relates to compounds and a method for their use in carrying physiologically active agents through body membranes such as skin and for retaining these agents in body tissues. More specifically, the invention relates to carboxylic acid derivatives and salts thereof, which compounds are useful in topically administering a physiologically active agent to a human or animal via a composition comprising the agent and an effective amount of a compound represented by the general formulae:

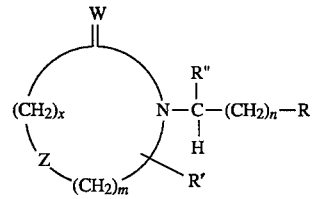

wherein W represents oxygen, sulfur, or two hydrogen radicals;

wherein Z represents oxygen, sulfur, or —$CH_2$—;

wherein R represents alkyl optionally substituted with one to three double or triple bonds, —SR''', —OR''', —NHR''', —$CH_3$, or $COOR_1$, and wherein $R_1$ represents hydrogen or lower alkyl;

wherein R''' represents alkyl, alkylthioalkyl, alkoxyalkyl, substituted aminoalkyl, optionally substituted with a phenyl, benzoyl or heterocyclic group;

wherein R' represents hydrogen, alkyl, alkoxy, acyloxy, alkylthio, hydroxy, —$(CH_2)_y COOR_1$ and with y being between zero and 3, inclusive;

and wherein R" represents hydrogen or —$(CH_2)_y COOR_1$ such that when R" is hydrogen, then W is two hydrogen radicals and R' is not hydrogen; and when R' is hydrogen, then R" is not hydrogen;

and wherein m is between one and 5, preferably 2, 3, or 4, while n is between 1 and 24, preferably between 5 and 12, and x is zero or 1, inclusive.

In an alternative embodiment, the novel penetration enhancers include compounds represented by the general formula:

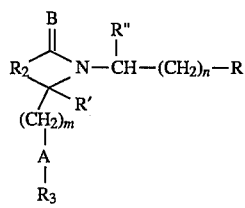

wherein B represents oxygen, sulfur, or two hydrogen radicals;

wherein A represents oxygen, sulfur, or —($CH_2$)—;

wherein R, $R_2$ and $R_3$ independently represent alkyl optionally substituted with 1 to 3 double or triple bonds, —SR''' —OR''' —NHR''' —$CH_3$ or $COOR_1$;

wherein R''' represents hydrogen, alkyl, alkylthioalkyl, alkoxyalkyl, submitted aminoalkyl, optionally substituted with a phenyl, benzoyl, or heterocyclic group;

wherein R' represents hydrogen, alkyl, alkoxy, acyloxy, alkylthio, hydroxy or —($CH_2$)$_y$$COOR_1$;

wherein R" represents hydrogen or —($CH_2$)$_y$$COOR_1$;

wherein $R_1$ represents a hydrogen or lower alkyl radical and y is between zero and 3, inclusive;

wherein m is between zero and 5, preferably 1 or 2; while n is between 1 and 24, preferably between 5 and 12, inclusive; and with the proviso that when R' and R" are both hydrogen, then R cannot be alkyl.

It should be understood in the above formula that peroxides, e.g., A=O and $R_3$=OR''', and nitroxides, e.g., A=O and $R_3$=NHR''', are not included as embodiments of the present invention.

And in yet another embodiment, the compound is represented by the formula:

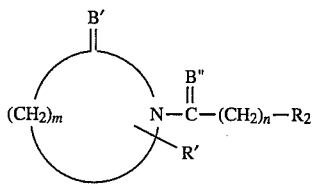

wherein $R_2$ is $COOR_1$ or an alkyl radical, optionally substituted with between 1 and 3 double or triple bonds;

wherein R' is a hydrogen radical, alkyl, alkoxy, acyloxy, alkylthio, hydroxy, or —($CH_2$)$_y$$COOR_1$;

wherein B' represents oxygen, sulfur, or two hydrogen radicals;

wherein B" represents oxygen, sulfur, or two hydrogen radicals such that when B" is not hydrogen, B' is two hydrogen radicals, and $R_2$ is alkyl, then R' is —($CH_2$)$_y$$COOR_1$ where y cannot be zero;

wherein y is between zero and three, inclusive, and $R_1$ represents a lower alkyl or hydrogen radical.

and wherein m is between 3 and 6, preferably 3, 4 or 5 while n is between 1 and 24, preferably between 5 and 12, inclusive;

and wherein y is between zero and three, inclusive, and $R_1$ represents a lower alkyl or hydrogen radical.

It has been found that physiologically active agents are carried through body membranes by the above penetration-enhancing agents and are retained in body tissue.

The invention further relates to the penetration-enhancing agents themselves and the method of making such penetration-enhancing agents.

DETAILED DESCRIPTION OF THE INVENTION

As used in this specification, the following terms are defined as set forth hereinafter:

"alkyl" means straight or branched chain alkyl having 1 to 16 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl (which includes "lower alkyl" which is $C_1$ to $C_{16}$ linear or branched alkyl);

"alkoxy" means straight or branched chain alkoxy having 1 to 16 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy, decyloxy, dodecyloxy, tetradecyloxy and hexacyloxy;

"alkylthioalkyl" means that the alkylthio moiety and the alkyl moiety each are straight or branched chain ones having 1 to 16 carbon atoms and 1 to 16 carbon atoms respectively and includes, for example, methylthiomethyl, ethylthiomethyl, propylthiomethyl, isopropylthiomethyl, butylthiomethyl, isobutylthiomethyl, tertiary butylthiomethyl, pentylthiomethyl, hexylthiomethyl, octylthiomethyl, 2-methylthioethyl, 2-ethylthioethyl, 2-butylthioethyl, 2-hexylthioethyl, 3-methylthiopropyl, 3-ethylthiopropyl, 3-propylthiopropyl, 3-butylthiopropyl, 4-methylthiobutyl, 4-ethylthiobutyl, 4-butylthiobutyl, 6-methylthiohexyl, 6-ethylthiohexyl, 6-butylthiohexyl, 8-methylthiooctyl, 8-ethylthiooctyl, 8-butylthiooctyl, 10-butylthiodecyl, 12-butylthiododecyl, 12-isobutylthiododecyl, 12-pentylthiododecyl and 16-butylthiohexadecyl;

"alkoxyalkyl" means that the alkoxy moiety and the alkyl moiety each are straight or branched chain ones having 1 to 16 carbon atoms and 1 to 16 carbon atoms and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexyloxyoctyl, 8-octyloxyoctyl, 10-butyloxydecyl, 12-butyloxydodecyl, 12-isobutyloxydodecyl, 16-butyloxyhexadecyl and 16-pentyloxyhexadecyl;

"aminoalkyl" means the aforesaid $C_1$ to $C_{16}$ alkyl groups attached to the group NH—or

when optionally substituted with a phenyl or benzoyl group.

Novel transdermal penetration enhancers useful in the method of the present invention include carboxylic acid derivatives and their salts, which are compounds represented by the general formulae:

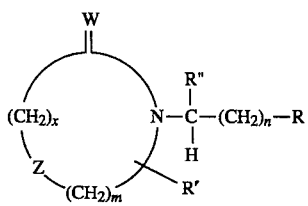

wherein W represents oxygen, sulfur, or two hydrogen radicals;

wherein Z represents oxygen, sulfur, or —CH$_2$—;

wherein R represents alkyl optionally substituted with one to three double or triple bonds, —SR''', —OR''' —NHR''', —CH$_3$, or COOR$_1$, and wherein R$_1$ represents hydrogen or lower alkyl;

and wherein R''' represents alkyl, alkylthioalkyl, alkoxyalkyl, substituted aminoalkyl, optionally substituted with a phenyl, benzoyl or heterocyclic group;

wherein R' represents hydrogen, alkyl, alkoxy, acyloxy, alkylthio, hydroxy, —(CH$_2$)$_y$COOR$_1$ and with y being between zero and 3, inclusive;

wherein R'' represents hydrogen or —(CH$_2$)$_y$COOR$_1$ such that when R'' is hydrogen, then W is two hydrogen radicals and R' is not hydrogen; and when R' is hydrogen, then R'' is not hydrogen;

and wherein m is between one and 5, preferably 2, 3, or while n is between 1 and 24, preferably between 5 and 12, inclusive, and x is zero or 1, inclusive.

In an alternative embodiment, the compounds useful as penetration enhancers include those represented by the general formula:

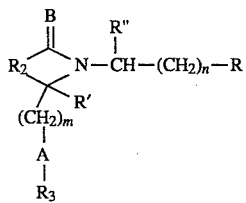

wherein B represents oxygen, sulfur, or two hydrogen radicals;

wherein A represents oxygen, sulfur or —(CH$_2$)—;

wherein R, R$_2$ and R$_3$ independently represent alkyl optionally substituted with 1 to 3 double or triple bonds, SR''', —OR''' —NHR''', —CH$_3$ or COOR$_1$;

wherein R''' represents hydrogen, alkyl, alkylthioalkyl, alkoxyalkyl, substituted aminoalkyl, optionally substituted with a phenyl, benzoyl, or heterocyclic group;

wherein R' represents hydrogen, alkyl, alkoxy, acyloxy, alkylthio, hydroxy, or —(CH$_2$)$_y$COOR$_1$;

wherein R'' represents hydrogen or —(CH$_2$)$_y$COOR$_1$;

wherein m is between zero and 5, preferably 1 or 2; while n is between 1 and 24, preferably between 5 and 12, inclusive;

wherein R$_1$ represents a hydrogen or lower alkyl radical and y is between zero and 3, inclusive; and with the proviso that when R' and R'' are both hydrogen, then R cannot be alkyl.

And in yet another embodiment the compound is represented by the formula:

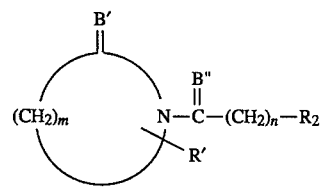

wherein R$_2$ is COOR$_1$ or an alkyl radical, optionally substituted with between 1 and 3 double or triple bonds and R$_1$ is hydrogen or lower alkyl;

wherein R' is a hydrogen radical, alkyl, alkoxy, acyloxy, alkylthio, hydroxy, or —(CH$_2$)$_y$COOR$_1$;

wherein B' represents oxygen, sulfur, or two hydrogen radicals;

wherein B'' represents oxygen, sulfur, or two hydrogen radicals such that when B'' is not hydrogen, B' is two hydrogen radicals, and R$_2$ is alkyl, then R' is —(CH$_2$)$_y$COOR$_1$ where y is not zero;

wherein y is between zero and three, inclusive, and R$_1$ represents a lower alkyl or hydrogen radical, and wherein m is between 3 and 6, preferably 3, 4, or 5, while n is between 1 and 24, preferably between 5 and 12, inclusive.

These novel transdermal penetration-enhancing additives may be made by the methods illustrated in the Examples below. Typical examples of compounds represented by the above general formulae include:

1-N-dodecyl-2-pyrrolidone-5-carboxylic acid
1-N-butyl-2-pyrrolidone-5-carboxylic acid
1-N-pentyl-2-pyrrolidone-5-carboxylic acid
1-N-hexyl-2-pyrrolidone-5-carboxylic acid
1-N-octyl-2-pyrrolidone-5-carboxylic acid
1-N-nonyl-2-pyrrolidone-5-carboxylic acid
1-N-decyl-2-pyrrolidone-5-carboxylic acid
1-N-tetradecyl-2-pyrrolidone-5-carboxylic acid
1-N-hexadecyl-2-pyrrolidone-5-carboxylic acid
1-N-heptyl-2-pyrrolidone-5-carboxylic acid
1-N-dodecyl-2-piperidone-6-carboxylic acid
1-N-butyl-2-piperidone-6-carboxylic acid
1-N-pentyl-2-piperidone-6-carboxylic acid
1-N-hexyl-2-piperidone-6-carboxylic acid
1-N-octyl-2-piperidone-6-carboxylic acid
1-N-nonyl-2-piperidone-6-carboxylic acid
1-N-decyl-2-piperidone-6-carboxylic acid
1-N-tetradecyl-2-piperidone-6-carboxylic acid
1-N-hexadecyl-2-piperidone-6-carboxylic acid
1-N-heptyl-2-piperidone-6-carboxylic acid
1-(2-(n-dodecylthio) ethyl)-2-pyrrolidone-5-carboxylic acid
1-(2-(n-butylthio) ethyl)-2-pyrrolidone-5-carboxylic acid
1-(2-(n-pentylthio) ethyl)-2-pyrrolidone-5-carboxylic acid
1-(2-(n-hexylthio)ethyl)-2-pyrrolidone-5-carboxylic acid
1-(2-(n-octylthio)ethyl)-2-pyrrolidone-5-carboxylic acid
1-(2-(n-nonylthio)ethyl)-2-pyrrolidone-5-carboxylic acid 1-(2-(n-decylthio)ethyl)-2-pyrrolidone-5-carboxylic acid
1-(2-(n-tetradecylthio)ethyl)-2-pyrrolidone-5-carboxylic acid
1-(2-(n-hexadecylthio)ethyl)-2-pyrrolidone-5-carboxylic acid
1-(2-(n-heptylthio)ethyl)-2-pyrrolidone-5-carboxylic acid
1-(2-(n-dodecylthio)ethyl)-piperidine-3-carboxylic acid
1-(2-(n-butylthio)ethyl)-piperidine-3-carboxylic acid
1-(2-(n-pentylthio)ethyl)-piperidine-3-carboxylic acid
1-(2-(n-hexylthio)ethyl)-piperidine-3-carboxylic acid
1-(2-(n-octylthio)ethyl)-piperidine-3-carboxylic acid
1-(2-(n-nonylthio)ethyl)-piperidine-3-carboxylic acid
1-(2-(n-decylthio)ethyl)-piperidine-3-carboxylic acid
1-(2-(n-tetradecylthio)ethyl)-piperidine-3-carboxylic acid
1-(2-(n-hexadecylthio)ethyl)-piperidine-3-carboxylic acid
1-(2-(n-heptylthio)ethyl)-piperidine-3-carboxylic acid
2-dodecyl,2—N-(2-pyrrolidone)-acetic acid
2-butyl,2—N-(2-pyrrolidone)-acetic acid
2-pentyl,2—N-(2-pyrrolidone)-acetic acid
2-hexyl,2—N-(2-pyrrolidone)-acetic acid
2-octyl,2—N-(2-pyrrolidone)-acetic acid
2-nonyl,2—N-(2-pyrrolidone)-acetic acid
2-decyl,2—N-(2-pyrrolidone)-acetic acid
2-tetradecyl,2—N-(2-pyrrolidone)-acetic acid
2-hexadecyl,2—N-(2-pyrrolidone)-acetic acid
2-heptyl,2—N-(2-pyrrolidone)-acetic acid
2-dodecyl,2—N-(2-piperidone)-acetic acid
2-dodecyl,2—N-(azacycloheptane-2-one)-acetic acid
2-butyl,2—N-(azacycloheptane-2-one)-acetic acid
2-pentyl,2—N-(azacycloheptane-2-one)-acetic acid
2-hexyl,2—N-(azacycloheptane-2-one)-acetic acid
2-octyl,2—N-(azacycloheptane-2-one)-acetic acid
2-nonyl,2—N-(azacycloheptane-2-one)-acetic acid
2-decyl,2—N-(azacycloheptane-2-one)-acetic acid
2-tetradecyl,2—N-(azacycloheptane-2-one)-acetic acid
2-hexadecyl,2—N-(azacycloheptane-2-one)-acetic acid
2-heptyl,2—N-(azacycloheptane-2-one)-acetic acid
6-(N-pyrrolidine)-hexanoic acid
8-(N-pyrrolidine)-octanoic acid
10-(N-pyrrolidine)-decanoic acid
12-(N-pyrrolidine)-dodecanoic acid
12-diethylaminododecanoic acid
10-diethylaminodecanoic acid
6-diethylaminohexanoic acid
8-diethylaminooctanoic acid
2-(N-morpholine)-2-dodecylacetic acid
2-(N-morpholine)-2-decylacetic acid
2-(N-morpholine)-2-octylacetic acid
2-(N-morpholine)-2-hexylacetic acid
2-(N-morpholine)-2-butylacetic acid
N-acetyl, N-dodecylalanine
N-ethyl, N-(1-oxododecyl)alanine
2-(N-ethylacetamido)-2-dodecylacetic acid
2-(N,N-diethylamino)-2-dodecylacetic acid
11-diethylaminoundecanoic acid
11-(N-ethylacetamido)undecanoic acid
N-acetyl-N-(10-carboxy-1-decyl)alanine It has also been found that the penetration-enhancers herein also themselves possess antiviral activity and can be used alone to combat viral infections.

When used in compositions comprising a second physiologically active agent, the amount of the novel transdermal penetration enhancers used in the present invention is an effective amount for enhancing percutaneous absorption. Generally, this amount ranges between about 0.01 to about 5 and preferably about 0.1 to 2 percent by weight of the composition.

The subject compositions may find use with many physiologically active agents which are soluble in the vehicles disclosed. The penetration enhancer can be applied before, after, or in combination with the physiologically active agent. The order of application is immaterial.

Fungistatic and fungicidal agents such as, for example, thiabendazole, chloroxine, amphotericin B, candicidin, fungimycin, nystatin, chlordantoin, clotrimazole, miconazole nitrate, pyrrolnitrin, salicylic acid, fezatione, tolnaftate, triacetin and zinc and sodium pyrithione may be dissolved in the penetration-enhancing agents described herein and topically applied to affected areas of the skin. For example, fungistatic or fungicidal agents so applied are carried through the stratum corneum, and thereby successfully treat fungus-caused skin problems. These agents, thus applied, not only penetrate more quickly than when applied in the vehicles of the prior art, but additionally enter the animal tissue in high concentrations and are retained for substantially longer time periods whereby a far more successful treatment is effected.

For example, the subject compositions may also be employed in the treatment of fungus infections on the skin caused by candida and dermatophytes which cause athletes foot or ringworm, by dissolving thiabendazole or similar antifungal agents in one of the above-described penetration-enhancing agents and applying it to the affected area.

The subject compositions are also useful in treating skin problems, for example, herpes simplex, which may be treated by a solution of iododeoxyuridine dissolved in one of the penetration-enhancing agents or such problems as warts which may be treated with agents such as podophyllin dissolved in one of the penetration-enhancing agents. Skin problems such as psoriasis may be treated by topical application of a solution of a conventional topical steroid in one of the penetration-enhancing agents or by treatment with theophylline or antagonists of β-adrenergic blockers such as isoproterenol in one of the penetration-enhancing agents. Scalp conditions such as alopecia areata may be treated more effectively by applying steroids such as triamcinolone acetonide dissolved in one of the penetrationenhancing agents of this invention directly to the scalp.

The subject compositions are also useful for treating mild eczema, for example, by applying a solution of fluocinolone acetonide or its derivatives; hydrocortisone, triamcinolone acetonide, indomethacin, or phenylbutazone dissolved in one of the penetration-enhancing agents to the affected area.

Examples of other physiologically active steroids which may be used with the vehicles include corticosteroids such as, for example, cortisone, cortodoxone, flucetonide, fluorocortisone, diflursone diacetate, flurandrenolone acetonide, medrysone, amcinafel, amcinafide, betamethasone and its esters, chloroprednisone, clocortelone, descinolone, desonide, dexamethasone, dichlorisone, defluprednate, flucloronide, flumethasone, flunisolide, fluocinonide, flucortolone, fluoromethalone, fluperolone, fluprednisolone, meprednisone, methylmeprednisolone, paramethasone, predisolone and prednisone.

The subject compositions are also useful in antibacterial chemotherapy, e.g. in the treatment of skin conditions involving pathogenic bacteria. Typical antibacterial agents which may be used in this invention include sulfonamides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, etc.

The subject compositions are also useful in protecting ultra-sensitive skin or even normally sensitive skin from damage or discomfort due to sunburn. Thus, dermatitis actinica may be avoided by application to the skin surfaces that are to be exposed to the sun of a sunscreen, such as para-aminobenzoic acid or its well-known derivatives in combination with one of the above-described penetration-enhancing agents. The protective para-aminobenzoic acid or its derivatives will thereby be carried into the stratum corneum more successfully and will therefore be retained even when exposed to water or washing for a substantially longer period of time than when applied to the skin in conventional vehicles. This invention is particularly useful for ordinary suntan lotions used in activities involving swimming because the ultraviolet screening ingredients in the carriers of the prior art are washed off the skin when it is immersed in water.

The subject compositions may also find use in treating scar tissue by applying topically to the scar tissue agents which soften collagen, such as aminopropionitrile or penicillamine dissolved in one of the penetration-enhancing agents of this invention.

Agents normally applied as eye drops, ear drops, or nose drops are more effective when dissolved in the penetration-enhancing agents of this invention.

Agents used in diagnosis may be used more effectively when applied dissolved in one of the penetration-enhancing agents of this invention. Patch tests to diagnose allergies may be effected promptly without scratching the skin or covering the area subjected to an allergen when the allergens are applied in one of the penetration-enhancing agents of this invention.

The subject compositions are also useful for topical application of cosmetic or esthetic agents. For example, compounds such as melanin-stimulating hormone (MSH) or dihydroxyacetone and the like are more effectively applied to skin to stimulate a suntan when they are dissolved in one of the penetration-enhancing agents of this invention. The agent is carried into the skin more quickly and in greater quantity when applied in accordance with this invention. Hair dyes also penetrate more completely and effectively when dissolved in one of the penetration-enhancing agents of this invention.

The effectiveness of such topically applied materials as insect repellents or fragrances, such as perfumes and colognes, can be prolonged when such agents are applied in combination with one of the penetration-enhancing agents of this invention.

It is to be emphasized that the foregoing are simply examples of physiologically active agents including therapeutic and cosmetic agents having known effects for known conditions, which may be used more effectively for their known properties in accordance with this invention.

In addition, the penetration-enhancing agents of the present invention may also be used to produce therapeutic effects which were not previously known. That is, by use of the penetration-enhancing agents described herein, therapeutic effects heretofore not known can be achieved.

As an example of the foregoing, griseofulvin is known as the treatment of choice for fungus infections of the skin and nails. Heretofore, the manner of delivery of griseofulvin has been oral. However, it has long been known that oral treatment is not preferred because of side effects resulting from exposure of the entire body to griseofulvin and the fact that only the outer layers of affected skin need to be treated. Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be delivered topically which would cause sufficient retention of griseofulvin in the skin to be useful therapeutically.

However, it has now been discovered that griseofulvin, in a range of therapeutic concentrations between about 0.1% and about 10% may be used effectively topically if combined with one of the penetration-enhancing agents described herein.

As a further example, acne is the name commonly applied to any inflammatory disease of the sebaceous glands; also acne vulgaris. The microorganism typically responsible for the acne infection is Corynebacterium acnes. Various therapeutic methods for treating acne have been attempted including topical antibacterials, e.g. hexachlorophene, and systemic antibiotics such as tetracycline. While systemic antibiotic treatments are known to be partially effective, topical treatments are generally not effective.

However, it has long been known that systemic treatment of acne is not preferred because of side effects resulting from exposure of the entire body to antibiotics and the fact that only the affected skin need be treated. Heretofore, despite a long-felt need for a topical treatment for acne, antibiotics generally have been used only systemically to treat acne because an antibacterial formulation which could be used topically as an effective therapeutic in the treatment of acne was not known. However, it has now been discovered that antibiotics, especially those of the lincomycin and erythromycin families of antibiotics, may be used topically in the treatment of acne if combined with one of the penetration-enhancing agents described herein.

The antibiotic compositions so applied are carried into and through the epidermis and deeper layers of the skin as well as into follicles, (which contain C. acnes) in therapeutically effective amounts and thereby successfully may be used to temporarily eliminate the signs and symptoms of acne.

The term "physiologically active agent" is used herein to refer to a broad class of useful chemical and therapeutic agents including physiologically active steroids, antibiotics, antifungal agents, antibacterial agents, antineoplastic agents, allergens, antihistaminic agents, anti-inflammatory agents, ultraviolet screening agents, diagnostic agents, perfumes, insect repellents, hair dyes, etc.

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freons, ethyl alcohol, polyvinylpyrrolidone, propylene glycol, fragrances, gel-producing materials, mineral oil, stearyl alcohol, stearic acid, spermaceti, sorbitan monooleate, "Polysorbates", "Tweens", sorbitol, methyl cellulose, etc.

The amount of the composition and/or of the physiologically active agent to be administered will obviously be an effective amount for the desired result expected therefrom. This, of course, will be ascertained by the ordinary skill of the practitioner. Due to enhanced activity which is achieved, the dosage of physiologically active agent may often be decreased from that generally applicable. In accordance with usual prudent formulating practices, a dosage near the lower end of the useful range of the particular physiologically active agent may be employed initially and the dosage increased as indicated from the observed response, as in the routine procedure of the physician.

The invention is further illustrated by the following examples which are illustrative of various aspects of the invention, and are not intended as limiting the scope of the invention as defined by the appended claims.

EXAMPLE 1

Preparation of
1-N-dodecyl-2-pyrrolidone-5-carboxylic acid

A. To a stirred solution of 1.92 g NaH (60%, washed with pet ether) in dry THF at room temperature under $N_2$ was added dropwise a solution of 7.06 g of ethyl 2-pyrrolidone-5-carboxylate in 20 mL of THF. The mixture was refluxed for 1 h, cooled to room temperature, followed by dropwise addition of 1.3 equivalents of 1-bromododecane. After additional reflux overnight and workup, the crude oil was subjected to flash chromatography (silica, 8:2 pet ether/EtOAc) to give 3.14 g of ethyl 1—N-dodecyl-2-pyrrolidone-5-carboxylate as a clear oil: NMR ($CDCl_3$) δ 4.2(m), 3.68(m), 2.9(m), 2.6–2.2(m), 2.1(m), 1.6–1.0(m), 0.9(t).

Basic hydrolysis of the product of example 1A at room temperature, followed by acidic workup resulted in 1.73 g of 1-dodecyl-2-pyrrolidone-5-carboxylic acid as a white solid: NMR ($CDCl_3$) δ 4.29 (m), 3.75 (m), 3.00 (m), 2.7–2.3 (m), 2.2 (m), 1.5 (m), 1.3(s), 0.9(t).

B. Example 1A was repeated using Ethyl 12-Bromododecanoate, followed by hydrolysis to give 12-(N-pyrrolidin-2-one-5-carboxy)dodecanoic acid.

C. Example 1A was repeated using Ethyl 2-Bromotetradecanoate, followed by hydrolysis to give 2-(N-pyrrolidin-2-one-5-carboxy)-2-dodecylacetic acid.

D. Example 1A was repeated replacing ethyl 2-pyrrolidone-5-carboxylic acid with proline ethyl ester, followed by hydrolysis to give N-dodecylproline.

E. Example 1A was repeated replacing ethyl-2-pyrrolidone-5-carboxylic acid with N-Acetyl alanine ethyl ester, followed by hydrolysis to give N-Acetyl-N-dodecylalanine.

F. Example 1A was repeated, replacing starting materials with N-ethyl alanine ethyl ester and dodecanoyl chloride and followed by hydrolysis to give N-Ethyl-N-(1-oxododecyl)alanine.

EXAMPLE 2

Preparation of 2-pentyl-2-oxo-1-pyrrolidineacetic acid

A. Alkylation of 2.0 g 2-pyrrolidone, under the same procedure described in Example 1A, with 7.23 g ethyl-2-bromoheptanoate resulted in 1.6 g of 2-pentyl-2-oxo-1-pyrrolidineacetic acid ethyl ester as a light yellow oil: NMR ($CDCl_3$) δ 4.75 (dd), 4.15 (q), 3.55 (m), 3.35 (m), 2.45 (t), 2.2–1.6 (m), 1.4–1.2 (m), 0.9 (m).

Basic hydrolysis of the product in Example 2A at room temperature, followed by acidic workup resulted in 0.8 g of 2-pentyl-2-oxo-1-pyrrolidineacetic acid as a white solid: NMR ($CDCl_3$) δ 4.8 (dd), 3.6 (m), 3.4 (m), 2.5 (t), 2.2–2.05 (m), 1.75 (m), 1.4–1.2 (s), 0.9 (t).

B. Example 2A was repeated using 2-Oxazolidine, followed by hydrolysis to give 2-dodecyl-2-oxa-3-oxazolidineacetic acid.

C. Example 2A was repeated using ε-Caprolactam and ethyl 2-bromotetradecanoate, followed by hydrolysis to give 2-(1-azacycloheptan-2-one) -2-dodecylacetic acid.

D. Example 2A was repeated using Morpholine, followed by hydrolysis to give 2-dodecyl-4-morpholineacetic acid.

E. Example 2A was repeated using Pyrrolidine, followed by hydrolysis to give 2-dodecyl-1-pyrrolidineacetic acid.

F. Example 2A was repeated using Proline ethyl ester, followed by hydrolysis to give 2-(N-pyrrolidino-2-carboxy)-2-dodecylacetic acid.

G. Example 2A was repeated using N-Ethyl acetamide, followed by hydrolysis to give 2-(N-ethylacetamido)-2-dodecylacetic acid.

H. Example 2A was repeated using Diethylamine, followed by hydrolysis to give 2-(N,N-diethylamino)-2-dodecylacetic acid.

I. Example 2A was repeated using ethyl 2-bromotetradecanoate, followed by hydrolysis to give 2-dodecyl-2-oxo-1-pyrrolidineacetic acid.

EXAMPLE 3

Preparation of 11-(diethylamino)-undecanoic acid

A. According to the previously described basic hydrolysis procedure of Example 1B, 0.47 g of ethyl 11-(diethylamino)-undecanoate resulted in the desired product as a white solid: NMR ($CDCl_3$) δ 3.1 (q), 2.95 (m), 2.25 (t), 1.7–1.6 (m), 1.4–1.1 (m).

B. Example 3A was repeated using Pyrrolidine, followed by hydrolysis, to give 11-(1-pyrrolidino)undecanoic acid.

C. Example 3A was repeated using Morpholine, followed by hydrolysis, to give 11-(4-Morpholino)undecanoic acid.

D. Example 3A was repeated using Piperazine, followed by hydrolysis, to give 11-(1-Piperazino)undecanoic acid.

E. Example 3A was repeated using 2-Pyrrolidinone, followed by hydrolysis, to give 11-(N-Pyrrolidino-2-one) undecanoic acid.

F. Example 3A was repeated using 2—Oxazolidone, followed by hydrolysis, to give 11-(3—Oxazolidin-2-one-)undecanoic acid.

G. Example 3A was repeated using ε-Caprolactam, followed by hydrolysis, to give 11-(1-hexamethylineimin-2-one) undecanoic acid.

H. Example 3A was repeated using Proline ethyl ester, followed by hydrolysis, to give 11-(1-pyrrolidin-2-carboxy)undecanoic acid.

I. Example 3A was repeated using N-Ethyl acetamide, followed by hydrolysis, to give 11-(N-Ethyl acetamido)-undecanoic acid.

J. Example 3A was repeated using N-Acetyl alanine ethyl ester, followed by hydrolysis, to give N-acetyl-N-(10-carboxy-1-decyl) alanine.

EXAMPLE 4

To model the capacity of the carboxylic acid derivatives of 1-substituted azacycloalkanes for enhancing permeability of physiologically active agents through skin and mucous membranes, a series of experiments were conducted using either ethanol-$C^{14}$ or butanol-$C^{14}$ as a control. The amount penetrating was calculated as percent of penetration of the control. For comparison with each control, parallel tests were also conducted using a known penetration enhancer, 1-n-dodecylazacyclo-heptane-2-one.

Ethanol and butanol have known permeability coefficients for passage through hairless mouse skin via a diffusion cell. The permeability coefficient is expressed by the formula:

$$P = \frac{DK_m/v}{h}$$

wherein D is the diffusivity (diffusion coefficient), $K_m/v$ is the partition coefficient between the membrane (m) and medium (v, vehicle), and h is the membrane thickness, respectively. See Kurihara-Bergstrom, T, et al., "Physiochemical Study of Percutaneous Absorption Enhancement by Dimethyl Sulfoxide: Kinetic and Thermodynamic Determinants of Dimethyl Sulfoxide Mediated Mass Transfer of Alkanols" in *Journal of Pharmaceutical Sciences*, Vol. 75, No. 5, May 1986, pp. 479–86. Full thickness abdominal and dorsal sections of mouse skin membranes were obtained from the hairless mouse strain (Skin Cancer Hospital, Temple University, Philadelphia, Penna.).

Formulations to be tested contained either one or five weight percent of a penetration enhancer, three weight percent Tween 20, and the balance of nanopure water. A trace amount of radio labelled ethanol $C^{14}$ or butanol $C^{14}$ was added to each formulation prior to assay and then 10 ml of the labelled formulation was counted in a liquid scintillation counter to determine the number of disintegrations per minute (DPM).

The receptor cells of nine finite dose Franz diffusion cells were filled with isotonic saline and maintained at 37° C. by submersion into a thermostatically controlled water jacket. The saline was stirred for 30 minutes with a magnetic stir bar to achieve equilibrium.

Freshly excised full thickness mouse skin was then mounted with an O ring between the donor and the receptor cells. After one hour of equilibration, the saline was removed from the receptor cells and replaced by 4–5 ml of fresh saline solution at 37° C.

Three of the nine donor cells were charged with 100 μl of radio-labelled saline containing no penetration enhancer as the control, three were charged with 100 μl of the one weight percent penetration enhancer formulation in labelled saline, and three cells were charged with equal amounts of the five weight percent penetration enhancer formulation in labelled saline.

At 45 minute intervals, 50 μl samples were taken from each receptor cell port with a micropipettor. The volume removed was replaced with a 50 μl sample of fresh 37° C. saline formulation. Each sample was then placed into a liquid scintillation counting vial along with 4.0 μl of scintillation cocktail (Aquasol, New England Nuclear, Boston, Mass.).

Based upon the predetermined DPM for each formulation, the amount of alkanol carried through the mouse skin by each formulation was calculated using known methods.

Tables II and III below summarize the increase in permeation of radio labelled alkanol achieved by addition of the penetration enhancer. It will be noted that in every test the penetration of ethanol was increased by at least 76 per cent over that achieved without aid of the penetration enhancers of this invention. The best results in these tests were achieved using a 1 weight percent concentration of N-0917 penetration enhancer, which yielded a penetration of ethanol through hairless mouse skin of 616% of that achieved without the penetration enhancer.

As shown in Table II, all of the penetration enhancers of this invention yielded penetration of butanol at least 119 percent of that achieved by the control.

TABLE I

ETHANOL - $C^{14}$ AS PERMEANT

| COMPOUND | CONC'N | PENETRATION COEFFICIENT ($\times 10^{-3}$ CM/NR) | % OF CONTROL |
|---|---|---|---|
| 1A | 1% | 19.42 | 616 |
|    | 5% | 17.20 | 546 |
| 2A | 1% | 8.21 | 155 |
|    | 5% | 25.62 | 484 |
| 2I | 1% | 11.28 | 341 |
|    | 5% | 6.89 | 208 |
| 2C | 1% | 2.38 | 76 |
|    | 5% | 4.82 | 155 |
| AZONE | 1% | 10.69 | 269 |
|       | 5% | 18.58 | 466 |

TABLE II

BUTANOL - $C^{14}$ AS PERMEANT

| COMPOUND | CONC'N | PENETRATION COEFFICIENT ($\times 10^{-3}$ CM/NR) | % OF CONTROL |
|---|---|---|---|
| 1A | 1% | 37.39 | 297 |
|    | 5% | 40.74 | 324 |
| 2A | 1% | 14.69 | 135 |
|    | 5% | 22.23 | 204 |
| 2I | 1% | 18.91 | 204 |
|    | 5% | 23.68 | 255 |
| 2C | 1% | 10.80 | 119 |
|    | 5% | 11.65 | 128 |
| AZONE | 1% | 24.83 | 340 |
|       | 5% | 23.29 | 319 |

EXAMPLE 5

The following formulation is prepared:

|  | Solution (%) |
|---|---|
| Griseofulvin | 1 |
| N-dodecyl-2-pyrrolidone-5-carboxylic acid | 1 |
| Isopropyl myristate | 5 |
| Fragrance | 0.1 |
| Ethanol | 92.9 |

This formulation is effective in the treatment of fungus infections.

EXAMPLE 6

An aerosol form of the formulation of Example 7 is prepared by preparing the following mixture:

| Formulation | 25% |
|---|---|
| Freon[1] | 75% |

[1]Freon is 75/25 Freon 114/12.

EXAMPLE 7

The following cream formulation is prepared:

| | % |
|---|---|
| Clindamycin base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| N-dodecyl-2-pyrrolidone-5-carboxylic acid | 0.5 |
| Sorbitol solution, U.S.P. | 5.5 |
| Sodium citrate | 0.5 |
| Chemoderm #844 Fragrance | 0.2 |
| Purified water | 68.4 |

This formulation is effective in the treatment of acne.

EXAMPLE 8

The following solution formulations are prepared:

| | A (%) | B (%) |
|---|---|---|
| Clindamycin base | — | 1.0 |
| Clindamycin phosphate acid | 1.3 | — |
| Sodium hydroxide | 0.077 | — |
| 1.0M Hydrochloric acid | — | 2.27 |
| Disodium edetate.2H$_2$O | 0.003 | 0.003 |
| Fragrances | 0.5 | 0.5 |
| N-dodecyl-2-pyrrolidone-5-carboxylic acid | .0 | 1.0 |
| Purified Water | 20.0 | 17.73 |
| Isopropanol | 77.12 | 77.497 |

These solutions are effective for the treatment of acne in humans.

EXAMPLE 9

The following solution formulation is prepared:

| | % |
|---|---|
| Neomycin sulfate | 0.5 |
| Lidocaine | 0.5 |
| Hydrocortisone | 0.25 |
| N-dodecyl-2-pyrrolidone-5-carboxylic acid | 0.5 |
| Propylene glycol | 98.25 |

This solution is effective for the treatment of otitis in domestic animals.

EXAMPLE 10

The following sunscreen emulsion is prepared:

| | % |
|---|---|
| p-Aminobenzoic acid | 2.0 |
| Benzyl alcohol | 0.5 |
| N-dodecyl-2-pyrrolidone-5-carboxylic acid | 1.0 |
| Polyethylene glycol 500-MS | 10.0 |
| Isopropyl lanolate | 3.0 |
| Lantrol | 1.0 |
| Acetylated lanolin | 0.5 |
| Isopropyl myristate | 5.0 |

-continued

| | % |
|---|---|
| Light mineral oil | 8.0 |
| Cetyl alcohol | 1.0 |
| Veegum | 1.0 |
| Propylene glycol | 3.0 |
| Purified water | 64.0 |

EXAMPLE 11

The following antineoplastic solution is prepared:

| | % |
|---|---|
| 5-Fluorouracil | 5.0 |
| N-dodecyl-2-pyrrolidone-5-carboxylic acid | 0.1 |
| Polyethylene glycol | 5.0 |
| Purified water | 89.9 |

EXAMPLE 12

The following insect repellant atomizing is prepared:

| | % |
|---|---|
| Diethyltoluamide | 0.1 |
| N-dodecyl-2-pyrrolidone-5-carboxylic acid | 0.1 |
| Ethanol | 99.8 |

EXAMPLE 13

The following lotion formulation may be prepared containing about 0.001 to 1 percent, with preferably 0.1 percent fluocinolone acetonide:

| | % |
|---|---|
| Fluocinolone acetonide | 0.001–1 |
| Cetyl alcohol | 15.0 |
| Propylene glycol | 10.0 |
| Sodium lauryl sulfate | 15.0 |
| N-dodecyl-2-pyrrolidone-5-carboxylic acid | 1.0 |
| Water (to make 100%) | |

The steroid is dissolved in the vehicle and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of the steroid into the inflamed tissue is enhanced and a therapeutic level is achieved more rapidly and sustained for longer duration than when the steroid is applied in conventional formulations.

The penetration enhancers of the present invention can also be used in combination with fabric dyes for the dyeing of fibers, additives, or textile auxiliaries, useful in improving or enhancing the dyeing process by enabling the dyeing of fibers at lower temperatures and in shorter times than without the use of the composition. Dyeable fibers include both natural and man-made fibers.

Natural fibers suitable for use in the method of the present invention include cotton, linen, wood, and silk and others such as kapok, hemp, jute and ramie. Man-made fibers include rayon (fibers composed of regenerated cellulose), acetate (fibers composed of cellulose approximately di- or tri-acetate) and synthetic fibers which are composed of nonnatural fiber-forming substances manufactured by chemical methods, such as polyamide, acrylic, polyester and polyolefin.

Typical polyamide fibers include nylons, such as, for example, poly (hexamethylene-adipamide), poly (mxylylene adipamide), poly (xylylene sebacamide), polycaprolactam and the like. Typical acrylic fibers are synthetic consisting wholly of polyacrylonitrile or a copolymer of a mixture of acrylonitrile and another vinyl compound, such as Orlon, Dynel, Verel, Creslan, Acrilan, Courtelle and Vinyon. Typical polyester fibers include Terylene, Dacron and Kodel. Typical polyolefin fibers include polyethylene, polypropylene, Vinylon, Rhouyl, Zefran and Darvan.

Various dyestuffs are available and may be classified as substantive or direct dyes, azoic or naphthol dyes, vat dyes and sulfur dyes, acid dyes and mordant or metalized dyes, basic or cationic dyes, disperse dyes and fiber reactive dyes.

Direct dyes are soluble in water and are applied primarily to cellulosic fibers and occasionally to protein fibers and polyamides, azoic or naphthol dyes are somewhat similar to developed direct dyes and are used on the same fiber group. Acid dyes and mordant or metalized dyes are used in protein fibers, acrylic fibers, nylon fibers and some modified polyester fibers. Cationic or basic dyes are used especially for coloring acrylic fibers and may be useful with nylon and polyester fibers. Disperse dyes were originally developed for use on acetate fibers and are now used for coloring acetate, polyester, acrylic and polyamide fibers. Reactive dyes are used primarily on cotton, cellulosis, wool, silk and acrylics.

While it is usual to dye most natural fibers in dye liquors at temperatures up to 100° C., these conditions are generally not sufficient to allow the production of deep shades on synthetic fiber materials. Furthermore, while some natural fibers, such as wool, can be satisfactorily dyed in boiling aqueous dye liquors, it usually takes 1½ to 2 hours for the dye to be fully absorbed to produce a deep shade. Wool dyes more slowly than cotton and viscose rayon. For this reason, it is generally not practical to dye wool fabrics by conventional continuous dyeing methods. However, at temperatures above 100° C., wool and synthetic fibers absorb dyes more quickly and thus the continuous dyeing of wool would be possible, except that such high temperature dyeing conditions can result in deterioration of the fiber.

With the use of the compounds described herein, the dyeing process can often be carried out at lower temperatures and completed in a shorter time than without the use of such compounds. Furthermore, use of the compounds described herein enhances the penetration of the dyes into the fiber being dyed and improves fastness. The compounds described herein are especially useful in the dyeing of synthetic fibers for carpet.

The amount of the compounds described herein which may be used in the present invention varies with the desired fiber and dye, the desired time and temperature of dyeing, and the dyeing process that is used. Generally, the compounds described herein may be used in amounts of about 0.1 to about 50% by weight and preferably about 1 to about 10% by weight of the dye liquor.

The textile materials with which the compounds of the present invention may be used may be of any type including, but not limited to, a yarn or fabric of any of the known fabric types including woven, knitted, or nonwoven. An especially suitable fabric is a tufted or looped pile carpet.

As used herein, the term "effective amount" in reference to the textile auxiliary disclosed herein, has reference to that amount of the disclosed compound sufficient to improve dye penetration by swelling the fibers to be dyed or dispersing the dye being used in the dyeing process into smaller particles for improving dye fastness, or facilitating the use of lower temperatures and shorter times in the dyeing process.

The subject composition is useful in the treatment of plants, in particular for an improved method of the delivery of plant nutrients.

The supply and absorption of chemical compounds needed for growth and metabolism may be defined as nutrition and the chemical compounds required by an organism termed nutrients. The mechanisms by which nutrients are converted to cellular material or used for energetic purposes are metabolic processes. The term 'metabolism' encompasses the various reactions occurring in a living cell in order to maintain life and growth. Nutrition and metabolism are thus very closely interrelated.

The essential nutrients required by green plants are exclusively of inorganic nature. In this respect, green plants differ fundamentally from man, animals and a number of microorganisms, which additionally need organic compounds as foodstuffs. An essential element may be defined as one which is required for the normal life cycle of an organism and whose functions cannot be substituted by other chemical compounds. In addition, the element must be shown to be directly involved in nutrition, as for example as a constituent of an essential enzyme system. Based on this definition, the following chemical elements are now known to be essential for higher plants:

| Carbon | C | Potassium | K | Zinc | Zn |
|---|---|---|---|---|---|
| Hydrogen | H | Calcium | Ca | Molybdenum | Mo |
| Oxygen | O | Magnesium | Mg | Boron | B |
| Nitrogen | N | Iron | Fe | Chlorine | Cl |
| Phosphorus | P | Manganese | Mn | Sodium | Na |
| Sulfur | S | Copper | Cu | Silicon | Si |
| Cobalt | Co | | | | |

The list of essential elements shown above may well not be complete and other elements, in very low concentrations, may yet be shown to be essential for higher plants. For some microorganisms, for example, vanadium (V) has now been established as an essential element.

The plant nutrients may be divided into macronutrients and micronutrients. Macronutrients are found and needed in plants in relatively higher amounts than micronutrients. The plant tissue content of the macronutrient N, for example, is over a thousand times greater than the content of the micronutrient Zn. Following the classification based on the element content in plant material, the following elements may be defined as macronutrients: C, H, O, N, P, S, K, Ca, Mg, Na and Si. The micronutrients are: Fe, Mn, Cu, Zn, Mo, B and Cl. This division of the plant nutrients into macro and micronutrients is somewhat arbitrary and in many cases differences between the contents of macronutrients and micronutrients are considerably lower than the example cited above.

The process of nutrient uptake and assimilation by plants is not fully understood, although a number of theories of ion uptake and transport are known, see for example, Mengel, et al., *Principles of Plant Nutrition*, Chapter 3, "Nutrient Uptake and Assimilation" International Potash Institute, Bern (1978).

The amount of the subject composition which may be used in the present invention is an amount effective for enhancing the delivery of a plant nutrient to a plant. Generally, an effective amount ranges between about 0.01 to about 99.9 and preferably about 0.1 to 10 percent by weight of the composition.

Plant nutrients which may be used in this invention include conventional macronutrients and micronutrients previously described including essential as well as nonessential plant nutrients. Examples of nutrients include, but are not limited to, the primary plant foods: nitrogen including ammonia and nitrate ions, phosphorous (phosphoric acid), potassium (potash); the secondary plant-food elements: calcium, magnesium and sulfur; and the trace elements: manganese, boron, copper, zinc, iron molybdenum and chlorine. The form of the foregoing nutrients may be in any conventional form, see, for example, McVickar, et al., *Using Commercial Fertilizer*, The Interstate Publishers, Danville, Ill. (1978).

The method of application of the plant nutrient compositions described herein is conventional. See, for example, McVickar, et al., *Using Commercial Fertilizers*, Chapter XIV, "Methods of Applying Fertilizers".

The precise amount of the plant nutrient composition to be delivered to the plant will obviously be an effective amount for the desired result expected therefrom. This, of course, will be ascertained by the ordinary skill of the practitioner. Due to enhanced activity which is achieved, the amount of plant nutrients may often be decreased from that generally applicable. In accordance with the usual prudent formulating practices, a dosage near the lower end of the useful range of the particular agent may be employed initially and the dosage increased as indicated from the observed response.

The subject composition as hereinabove described in combination with a pesticide, provides a method and composition for plant pest control.

Pesticides are chemicals designed to combat the attacks of various pests on agricultural and horticultural crops. They fall into three major classes: insecticides, fungicides and herbicides (or weed killers). There are also rodenticides (for control of vertebrate pests), nematicides (to kill microscopic eelworms), mollusicides (to kill slugs and snails) and acaricides (to kill mites).

Pesticides may also be divided into two main types, namely contact or nonsystemic pesticides and systemic pesticides. Contact or surface pesticides do not appreciably penetrate plant tissues and are consequently not transported or translocated, within the plant vascular system. The earlier insecticides, fungicides and herbicides were of this type; their disadvantages are that they are susceptible to the effects of weathering (wind, rain and sunlight) over long periods and new plant growth will be left unprotected and hence open to attack by insect and fungal pests. The early agricultural fungicides were, therefore, protectant fungicides—in other words, they are designed to prevent the development of the fungal spores, but once the fungus has become established and infection starts to ramify through the plant tissues, such nonsystemic fungicides possess little eradicant action and usually cannot halt the infection.

In contrast, many of the more recent pesticides are systemic in character; these can effectively penetrate the plant cuticle and move through the plant vascular system. Examples are provided by the phenoxyacetic acid selective herbicides, certain organophosphorus insecticides and the more recently discovered systemic fungicides like benomyl.

Systemic fungicides are also sometimes termed plant chemotherapeutants and cannot only protect the plant from fungal attack, but also cure or inhibit an established infection. They are little affected by weathering and will also confer immunity on all new plant growth.

Pests can be divided into various groups. In the plant kingdom, characterized by the ability of the organism to photosynthesize carbohydrates from air and water with the aid of the green pigment chlorophyll, higher plants growing where man does not want them are termed weeds and are important pests. Of the lower plants, algae are not generally of as great importance as pests, although in some circumstances, e.g., in lakes and other slow-moving water, excessive algal growth of "bloom" may cause considerable damage and require treatment with chemicals (algicides).

Fungi or nonphotosynthetic plants cannot obtain their nutrients from air and water since they do not have chlorophyll; consequently, they feed directly on decaying plant or animal matter (saprophytic fungi) or on living plants or animals (parasitic fungi). There are thousands of different species of fungi mainly found in soil; some, like yeasts, are unicellular while others are composed of a network of branched filaments (hyphae). A number of fungi are serious pests attacking both living crop plants and also crops in storage.

Several bacteria are causal agents of plant diseases, although they are not nearly as important as the phytopathogenic fungi. Bacteria can be observed under the microscope and can be classified according to their shape; thus a spherical bacterium is termed a coccus while a rodshaped one is a bacillus.

Viruses, like bacteria and fungi, attack plants and animals and some species cause significant plant diseases. Viruses form a distinct category of living organism because they are not true cells. Unlike bacteria, they are too small (100–300 A) in diameter to be observed with an ordinary microscope, but they can be revealed under the electron microscope; each virus consists of a single strand of DNA or RNA surrounded by a protective coat of protein.

Several higher animals (vertebrates) are important pests, e.g., mice, rats and rabbits; another group of pests is represented by the true insects (arthropods) which are invertebrates. The latter possess three pairs of legs and the adult body has three parts; the arachnids (mites and ticks) differ from true insects in having no distinct division of the body into three parts; also they usually have four pairs of legs. In the lower orders of animals, certain nematodes, parasitic worms often with unsegmented bodies, are important crop pests.

If pesticides are to be active, they must reach the ultimate site of action within the target organism. Thus, even surface fungicides, like Bordeaux mixture, must be able to penetrate the fungal spore; similarly, contact insecticides have to penetrate the insect cuticle, and contact herbicides penetrate the plant cuticle when they impinge on it. The requirements if the pesticides are to be systemic in action are much more stringent because, in addition, they must have the capacity to be absorbed by the roots or leaves or seeds of plants and be delivered to other parts of the plant. In this way, the whole plant, including new growth, is protected from fungal attack, or rendered poisonous to any insect that eats or sucks it.

The amount of the subject composition which may be used in the present invention is an amount effective for enhancing the delivery of a pesticide to a plant pest. In the case of indirect application of the active materials to a plant, the enhanced delivery achieved through the use of 1-substituted azacycloalkane includes improved substantivity and systemic effects of the pesticide. Generally, an effective amount ranges between about 0.01 to about 99.9 and preferably about 0.1 to 10 percent by weight of the pesticide composition.

Suitable pesticides include botanical insecticides such as, for example, nicotine, derris (rotenone) and pyrethrum; synthetic insecticides including dinitrophenols, such as, for example, DNOC; organic thiocyanates such as, for example, lethane and thanite, organochlorine insecticides including DDT and related compounds; containing the cyclodiene group such as, for example, aldrin and dieldren, organosphosphorous insecticides; hexachlorocyclohexane; insecticides including malathion, mevinphos, rogar, dimethtoate, nenozan, miral, diazinon, dursbon, bay-rusil; organocarbonate insecticides including pirimicarb, carbaryl, baygon, propoxur, zectron, carbofuran, aldicarb (Temik), methomul (Lonnate); fungicides including phenylmercury compounds, naban, metham, sodium, thiron; compounds containing the n-trichloromethylthio group, such as, for example, captan, folpet and oifolatan; dinitrophenols, including dinocap (Karathane); chlorobenzynes and related compounds, quinones such as, for example, dodine and roural, sulphonamides, benzimidazoles; thiophonates; oxathinns; pyrimadines; piperozine, morpholine and azepine derivatives; organophosphorous compounds including wepsyn, kitazin and conen, herbicides including carboxylic acid herbicides, such as, for example, 2, 4-D MCPA, 2, 3, 6-TBA, IAA, picloram and dichlobenil; chloroaliphatic acids such as dalapan and TCA, and heterocyclic compounds such as atrozine (Gesaprim); triazales such as amitrole, pyrazon, bromacil, endothal; bipyridinum herbicides including paraquat and diquat; benzonitriles; diphenyl ethers; organosphosphorous compounds such as, for example, phosphorothiolates such as bensullide; phosphoramidates such as DMPA (Zyron); phosphonates such as glyphosate; plant growth regulators; fumigants; rodenticides including anticoagulants such as warfarin, pidone and norbormide (Raticote); sleep-inducing narcotic drugs such as chloralose; gophacide, silatrane and crimidine, nematicides such as dazomet and nellite; molusicides such as metaldehyde, methiocasb and frescon; repellants, antifeeding compounds such as ZIP; chemosterilants, hormones and growth inhibitors. Further examples of pesticides suitable for use in the present invention are known in the art (see, for example, R. Cremyln, *Pesticides, Preparation and Mode of Action,* John Wiley and Sons, 1979; F. McEwan, et al., *The Use of Significance of Pesticides in the Environment,* John Wiley and Sons, 1979; D. Roberts, *Fundamentals of Plant Pest Control,* E. H. Freeman and Company, 1978.

The method of application of the pesticide composition described herein is conventional. See, for example, G. Hartley, et al., *Chemicals for Pest Control,* Chapter 15, "Application of Pesticides," Pergamon Press, 1969.

The precise amount of the pesticide composition to be delivered to the plant or pest will obviously be an effective amount for the desired result expected therefrom. Most modern pesticides are used in agriculture at a dosage of less than one pound per acre. This, of course, will be ascertained by the ordinary skill of the practitioner. Due to enhanced activity which is achieved, the dosage of agent may often be decreased from that generally applicable. In accordance with the usual prudent formulating practices, a dosage near the lower end of the useful range of the particular agent may be employed initially and the dosage increased as indicated from the observed response.

The subject composition as hereinabove described, in combination with a plant growth regulator, is a method and composition for plant growth.

Plant growth regulators are organic compounds, other than nutrients, that, in low concentrations, affect the morphological structure and/or physiological processes of plants. Plant hormones or phytohormones, are naturally occurring growth regulators that in low concentrations control physiological processes in plants. The synthetic growth regulators are used by Man to control such processes as fruit development, fruit thinning, defoliation, growth stimulation and retardation, rooting of cuttings and many other processes. Over the past 30 years, the investigation and development of plant growth regulators has been one of the most active areas of fundamental and applied botanical research. The PANS Plant Growth Regulator Index (P. J. Kempt, 25 (2), 211 and 213) under the list of Common and Trade Names and Code Numbers has 492 entries (excluding herbicides except where these are used specifically for some growth regulatory purpose other than weed killing).

Plant growth regulators that are currently in use at the present time affect a great variety of plant growth processes, including the following (some of the growth regulators in common use are in brackets): rooting of cuttings (indolebutyric acid); promotion of flowering in pineapples (1-naphthaleneacetic acid; B-hydroxyethylhydrazine; ethephon); prevention of preharvest drop of apples (NAA; daminozide); inhibition of turf growth (maleic hydrazide; mefluididediethanolamine); prevention of sprouting of potatoes (maleic hydrazide); floral induction in apple, pear, peach (succinic acid-2, 2-dimethylhydrazine; 2, 3, 5-triodobenzoic acid); early flowering of 'long day' plants, e.g., lettuce radish, mustard, dill (gibberellins); flowering of many biennials which normally require low temperatures to flower (gibberellins); improvement of yield of sugar-cane and prevention of flowering (diuron; diquat); delay in flowering in almond and peach to avoid adverse weather conditions (diaminozide); induction of abscission of mature citrus fruits (cyclohexim; 5-chloro-3-methyl-4-nitro-1-H-pyrazole); defoliation of cotton leaves to aid harvesting of bolls (ethephon); thinning of fruit, e.g., grapes, peaches, (gibberellic acid; ethephon, 3-chlorophenoxy-α-propionamide); prevention of pre-harvest drop of citrus (2, 4-dichlorophenoxyacetic acid); induction of fruit set, e.g., in tomato, squash, eggplant, fig (4-chloro-phenoxyacetic acid; 2-naphthyloxy-acetic acid); increase in size and quality of grapes (gibberellins); induction of amylase in barley for malting (gibberellins); stimulation of growth of sugar-cane (gibberellins); reduction of stem length in cereals (2-chloroethyl trimethylammonium chloride); development of female flowers, e.g., in pumpkins (NAA; ethephon; daminozide); promotion of male flowers, e.g., in hops (gibberellins); bioregulation of plant composition, e.g., color in citrus, sugar in sugar-cane, vitamin content in vegetables, increase in dry weight, timing of crop development, increased latex from rubber trees (various growth regulators).

The amount of the subject composition which may be used in the present invention is an amount effective for enhancing the delivery of a plant growth regulator to a plant. Generally, an effective amount ranges between about 0.01 to about 99.9 and preferably about 0.1 to 10 percent by weight of the composition.

Suitable plant growth regulators include both natural and synthetic auxins, such as IAA (indolyl-3-acetic acid), IBA (4-(indol-3 yl) butyric acid), NAO (alphanaphthylacetic acid), NOA (2-naphthyloxy-acetic acid) and NAD (1-naphthylacetamide); phenoxyalkanoic acids, gibberellins, cytokinins, abscisic acid, maleic hydrazide, propham and cloropopham, S,S,S-tributyl phosphorotrithioate, S,S,S, Tributyl phosphorotrithioite, chloromequat, daminozide, glyphosine, ancymidol, chlorphonium chloride, dikegulac sodium, morpholinium chloride, fosamine, mefulidide, 4-methoxybenzophenones, PP 528 (ethyl-5-(4-chlorophenyl) -2H-tetrazol-2-yl acetate), piproctanyl bromide, 2-(3-aryl-5-pyrazoyl) benzoic acids, BTS 34723 (1-(N-2-phenoxyethyl)-N-propylcarbamoy)-N-imidazole), BTS 34442 (1-(N-2,4-dichlorobenzyl)-N-isopropyl-carbamoyl)-1N-imidazole), UBI P293 (2,3,-dihydro-5, 6-diphenyl-1, 4-oxathiin), M&B 25, 105 (propyl 3-t-butyl phenoxyacetate), thidaizuron (N-phenyl-N'-(1,2,3-thiadiazol-5-yl) urea), mepiquat (1,1-dimethylpiperidinium chloride), BAS 09800W (mepiquat chloride plus ethephan), IZAA (5-chloroindazole-8-acetic ethyl ester), MON 8000, DOWCO 242 (tetraisopentyl-ammonium bromide), quarternary ammonium iodides; morphactins including chloroflurecol-methyl, flurecol-butyl, TIBA (2,3,5-tri-iodobenzoic acid; gametocides including RH 531 (sodium 1-(4-chlorphenyl)-1,2-dihydro-4, 6-dimethyl-2-oxonicotinate), DPX-3778 (3-(4-chlorophenyl)-6-methoxy-1,3,5-triazine-2, 4-dione triethanolamine) and allelopathins. Additional plant growth regulators are known in the literature, see, for example, Fletcher, et al., *Herbicides and Plant Growth Regulators*, Chapter 2.

Opportunities for use of plant growth regulators include treatments for seed or seedlings for transplanting which will promote early growth and root development; substances to improve quality (usually protein levels and amino acid balance) of grain crops; substances to improve yield and quality of forages; opportunities in forestry, such as seeding survival and growth, early seed production and accelerated growth rates; systems to reduce energy costs by maximizing response to cultivation, fertilizers (i.e., uptake, mobilization, etc.) and irrigation water; compounds to inhibit ethylene action or production and thus reduce young fruit abscission in indeterminately fruiting crops; new gibberellins with species- or function specific effects, new applications of known substances based on understanding hormone interactions and storage/inactivation systems ('slow release' compounds) and substances to manipulate natural conjugation reactions; substances to alleviate or minimize effects of plant diseases and insects, or to facilitate systems of integrated pest management; substances to modify productivity by reducing photorespiration, dark respiration, or by promoting nitrogen metabolism/fixation, photosynthesis, translocation; substances that intensify synthesis of specific highly desired end-products (oil, protein, cellulose); substance to increase productivity by shifting developmental patterns, such as extending the period of inflorescence differentiation or seed development. The foregoing serves to illustrate the wide range of opportunities available to agricultural chemists.

Plant tissue culture pioneered by White, Steward, Skoog and others, beginning almost as a botanical curiosity, has with the help of growth-regulatory chemicals become a powerful tool in the hands of the plant breeder. It is now possible to tissue culture almost any plant and to develop uniform plantlets from such cultures. Even pollen grains can be used and the subsequent haploid plants made polyploid by the use of suitable chemical agents. Together with apical meristem culture, there is an unending supply of material.

The method of application of the plant growth regulator composition described herein is conventional. See, for example, W. W. Fletcher and R. C. Kirkwood, *Herbicides and Plant Growth Regulators*, Granada Publishing Limited, New York, 1982.

The precise amount of the plant growth regulator composition to be delivered to the plant will obviously be an effective amount for the desired result expected therefrom. This, of course, will be ascertained by the ordinary skill of the practitioner. Due to enhanced activity which is achieved, the amount of plant growth regular may often be decreased from that generally applicable. In accordance with the usual prudent formulating practices, a dosage near the lower end of the useful range of the particular agent may be employed initially and the dosage increased as indicated from the observed response.

While particular embodiments of the invention have been described, it will be understood, of course, that the invention is not limited thereto since many obvious modifications can be made and it is intended to include with this invention any such modifications as will fall within the scope of the appended claims.

We claim:

1. A composition comprising an effective amount of a physiologically active agent selected from the group consisting of lincomycin, clindamycin, erythromycin and pharmaceutically acceptable salts thereof and an effective penetration enhancing amount of a compound represented by the formula:

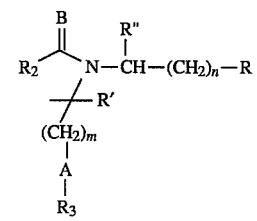

or the pharmaceutically acceptable salt thereof;

wherein B represents oxygen, sulfur or two hydrogen radicals;

A represents oxygen, sulfur or —CH$_2$—;

R, R$_2$ and R$_3$ independently represent (C$_1$–C$_{16}$)alkyl —Sr''', —OR''', —NHR''', or —COOR$_1$, where R$_1$ is hydrogen or (C$_1$–C$_{16}$)alkyl;

R''' represents hydrogen, (C$_1$–C$_{16}$)alkyl, (C$_1$–C$_{16}$)alkylthio(C$_1$–C$_{16}$)alkyl, (C$_1$–C$_{16}$)alkoxy(C$_1$–C$_{16}$)alkyl, amino(C$_1$–C$_{16}$)alkyl, optionally substituted with a phenyl, or benzoyl group;

R' represents hydrogen, (C$_1$–C$_{16}$)alkyl,(C$_1$–C$_{16}$)alkoxy, (C$_1$–C$_{16}$)alkylthio, hydroxy, or —(CH$_2$)$_y$COOR$_1$, and further wherein y is between 0 and 3, inclusive;

R'' represents hydrogen or —(CH$_2$)$_y$COOR$_1$;

m is between 0 and 5, while n is between 1 and 24, inclusive; and with the proviso that when R' and R'' are both hydrogen, then R cannot be (C$_1$–C$_{16}$)alkyl.

2. The composition of claim 1 where R$_1$ is ethyl.

3. The composition of claim 1 where R$_1$ is methyl.

4. The composition of claim 1 where A is —CH$_2$—, R$_2$ is —CH$_3$, R$_3$ is —CH$_3$, m is zero, R' is hydrogen, B is two hydrogen radicals, R is —COOR$_1$ where R$_1$ is hydrogen, R'' is hydrogen, and n is nine.

5. The composition of claim 4 where R$_1$ is ethyl.

6. The composition of claim 4 where R$_1$ is methyl.

7. A composition comprising an effective amount of iododeoxyuridine and an effective penetration enhancing amount of a compound represented by the formula:

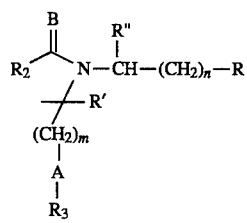

or the pharmaceutically acceptable salt thereof;

wherein B represents oxygen, sulfur or two hydrogen radicals;

A represents oxygen, sulfur or —$CH_2$—;

R, $R_2$ and $R_3$ independently represent ($C_1$–$C_{16}$)alkyl —SR''', —OR''', —NHR''', or —$COOR_1$ where $R_1$ represents hydrogen or ($C_1$–$C_{16}$)alkyl;

R''' represents hydrogen, ($C_1$–$C_{16}$)alkyl, ($C_1$–$C_{16}$)alkylthio($C_1$–$C_{16}$)alkyl, ($C_1$–$C_{16}$)alkoxy($C_1$–$C_{16}$)alkyl, amino($C_1$–$C_{16}$)alkyl, optionally substituted with a phenyl, or benzoyl group;

R' represents hydrogen, ($C_1$–$C_{16}$)alkyl, ($C_1$–$C_{16}$)alkoxy, ($C_1$–$C_{16}$)alkylthio, hydroxy or —$(CH_2)_y COOR_1$, and further wherein y is between 0 and 3, inclusive;

R'' represents hydrogen or —$(CH_2)_y COOR_1$;

m is between 0 and 5, while n is between 1 and 24, inclusive; and with the proviso that when R' and R'' are both hydrogen, then R cannot be ($C_1$–$C_{16}$)alkyl.

8. The composition of claim 7 where $R_1$ is ethyl.
9. The composition of claim 7 where $R_1$ is methyl.
10. The composition of claim 7 where A is —$CH_2$—, $R_2$ is —$CH_3$, $R_3$ is —$CH_3$, m is zero, R' is hydrogen, B is two hydrogen radicals, R is —$COOR_1$ where $R_1$ is hydrogen, R'' is hydrogen, and n is nine.
11. The composition of claim 7 where $R_1$ is ethyl.
12. The composition of claim 7 where $R_1$ is methyl.
13. A method for enhancing penetration of topically administered active agents through the skin or mucosal membranes of humans or animals comprises the topical administration to the skin or mucosal membrane of humans and animals of effective amounts of a physiologically active agent selected from the group of iododeoxyuridine and an effective penetration enhancing amount of a compound having the structural formula:

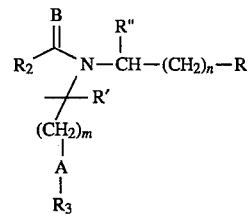

or the pharmaceutically acceptable salt thereof;

wherein B represents oxygen, sulfur or two hydrogen radicals;

A represents oxygen, sulfur or —$CH_2$—;

R, $R_2$ and $R_3$ independently represent ($C_1$–$C_{16}$)alkyl, —SR''', —OR''', —NHR''', or —$COOR_1$, where $R_1$ is hydrogen or ($C_1$–$C_{16}$)alkyl;

m is between 0 and 5 while n is between 1 and 24, inclusive;

R' represents hydrogen, ($C_1$–$C_{16}$)alkyl, ($C_1$–$C_{16}$)alkoxy, ($C_1$–$C_{16}$)alkylthio, hydroxy or —$(CH_2)_y COOR_1$;

R'' represents hydrogen or —$(CH_2)_y COOR_1$;

R''' represents hydrogen, ($C_1$–$C_{16}$)alkyl, ($C_1$–$C_{16}$)alkylthio($C_1$–$C_{16}$)alkyl, ($C_1$–$C_{16}$)alkoxy($C_1$–$C_{16}$)alkyl, amino ($C_1$–$C_{16}$)alkyl, optionally substituted with a phenyl, or benzoyl group and y is between 0 and 3, inclusive; and with the proviso that when R' and R'' are both hydrogen, then R cannot be ($C_1$–$C_{16}$)alkyl.

* * * * *